United States Patent
Oguri

(10) Patent No.: US 7,759,128 B2
(45) Date of Patent: Jul. 20, 2010

(54) HISTAMINE DETECTION METHOD AND HISTAMINE DETECTION KIT

(75) Inventor: Shigeyuki Oguri, Aichi (JP)

(73) Assignee: Nagoya Industrial Science Research Institute, Nagoya (JP)

( * ) Notice: Subject to any disclaimer, the term of this patent is extended or adjusted under 35 U.S.C. 154(b) by 672 days.

(21) Appl. No.: 11/596,676

(22) PCT Filed: Mar. 18, 2005

(86) PCT No.: PCT/JP2005/005628

§ 371 (c)(1),
(2), (4) Date: Dec. 5, 2006

(87) PCT Pub. No.: WO2005/114182

PCT Pub. Date: Dec. 1, 2005

(65) Prior Publication Data

US 2007/0243625 A1 Oct. 18, 2007

(30) Foreign Application Priority Data

May 20, 2004 (JP) ............................. 2004-150230

(51) Int. Cl.
*G01N 21/29* (2006.01)
*G01N 33/02* (2006.01)

(52) U.S. Cl. .............................. 436/164; 435/39; 436/1; 436/21

(58) Field of Classification Search ........................ None
See application file for complete search history.

(56) References Cited

U.S. PATENT DOCUMENTS

2004/0014235 A1 * 1/2004 Kelly et al. ................. 436/166

FOREIGN PATENT DOCUMENTS

| JP | A 61-219864 | 9/1986 |
| JP | A 10-170514 | 6/1998 |
| JP | A 2001-157597 | 6/2001 |
| JP | A 2003-61650 | 3/2003 |

OTHER PUBLICATIONS

Zhang et al., "Determination of histamine and histidine by capillary zone electrophoresis with pre-column naphthalene-2, 3-dicarboxaldehyde derivatization and fluorescence detection", *Journal of Chromatography*, vol. 1040, No. 1, pp. 133-140, May 10, 2004.

James et al., "Determination of histamine from plasma using derivatization with naphthalene 2, 3-dicarboxaldehyde and HPLC with fluorescence detection", *American Association of Pharmaceutical Scientists—1992 Annual Meeting and Exposition: Contributed Papers Abstracts*, San Antonio, Texas, APQ 1042, p. S-21, Nov. 15-19, 1992.

* cited by examiner

*Primary Examiner*—Krishnan S Menon
*Assistant Examiner*—Rebecca Fritchman
(74) *Attorney, Agent, or Firm*—Oliff & Berridge, PLC

(57) ABSTRACT

The histamine detection method of the invention includes: a reaction step of causing a sample solution possibly containing histamine to react with 2,3-naphathalene dicarboxylaldehyde at PH of less than 10; and a detection step of detecting histamine based on a color change in the reaction step. The arrangement of this histamine detection method ensures the good color development in a visible region and thus enables easy and quick detection of histamine.

9 Claims, 5 Drawing Sheets

HISTAMINE DETECTION METHOD AND HISTAMINE DETECTION KIT

TECHNICAL FIELD

The present invention relates to a histamine detection method and a histamine detection kit embodying the histamine detection method.

BACKGROUND ART

The safety of food is essential for effective prevention of food poisoning and other food-inducing infections. Histamine poisoning is one example of the food poisoning. As is well known, histamine is produced from free histidine by means of bacteria having histidine decarboxylase (mainly Morganella). Lean fish, such as tuna and mackerel, especially have the high histidine content as the precursor of histamine. Fish meat polluted with such bacteria may have large accumulation of histamine. Uptake of the polluted fish meat causes transient food poisoning. This food poisoning is called allergy-like food poisoning (histamine poisoning). The reported number of histamine poisoning cases is relatively small. A large number of unreported cases are, however, expected, because of the transient tendency of the histamine poisoning. The actual cases may thus amount to a considerable number.

Histamine is water-soluble and relatively stable to heat and is thus not decomposable for removal in the ordinal cooking process. Monitoring the histamine content is accordingly the most effective measure for prevention of the histamine poisoning. Histamine may be a control target in the HACCP sanitation management system.

Currently available methods take advantage of enzyme reactions to measure histamine contained in food (see Japanese Patent Laid-Open Gazette No. 2001-157597 and No. 2003-61650).

DISCLOSURE OF THE INVENTION

The enzyme reaction-based measurement, however, requires strict temperature and pH control for the sufficient reaction and rather complicated pretreatment, as well as specific instruments and reagents for the detection. These proposed methods take much time and labor and are not suitable for quick measurement of the histamine content in the course of catching fish as the material of marine products, distributing the fish, processing the fish to manufacture the processed marine products, or cooking the marine products at restaurants or other equivalent facilities. Easy and quick measurement of histamine has thus been demanded for effective safety and quality control of food with regard to histamine.

An object of the invention is to provide a histamine detection method for easy and quick detection of histamine, as well as a histamine detection kit embodying the histamine detection method. The invention also aims to provide a food sanitation management method of manufacturing a food product, for example, a marine product, with easy and quick monitoring and management of the histamine content in a food material or in the food product.

The inventors have examined the availability of color reactions for detection of histamine and have completed the present invention based on the finding of good color development in a visible region by a reaction of histamine with a specific compound, which may react with histamine to produce a fluorescent substance, under a no fluorescent substance-producing condition. The technique of the invention has various applications described below to attain at least part of the above and the other related objects.

The present invention is directed to a histamine detection method, which includes: a reaction step of causing a sample solution possibly containing histamine to react with 2,3-naphathalene dicarboxylaldehyde at PH of less than 10; and a detection step of detecting histamine based on a color change in said reaction step. The detection step detects the histamine preferably at wavelengths of not lower than 600 nm and not higher than 700 nm. In one preferable embodiment of the invention, the histamine detection method further has a supply step of feeding the sample solution to a histamine-supportable carrier, prior to the reaction step. In this embodiment, the reaction step makes histamine react with 2,3-naphathalene dicarboxylaldehyde on the carrier. The sample solution may be a fish meat exudate or a fish meat extract. In the histamine detection method of the invention, it is preferable that the detection step determines quantity of histamine corresponding to a level of the color change.

The present invention is also directed to a histamine detection kit, which includes: a 2,3-naphathalene dicarboxylaldehyde-containing reagent; and a reaction field providing module including a histamine-supportable carrier. In one preferable embodiment of the histamine detection kit, the reaction field providing module is a column for receiving the carrier therein. In another preferable embodiment of the histamine detection kit, the reaction field providing module has the carrier on at least one end thereof and a shape for holding function. In still another preferable embodiment of the histamine detection kit, the reaction field providing module is isolated from food but is formed as part of a packaging container of the food and works as an absorber for an exudate of the food. In any of these embodiments of the histamine detection kit, it is preferable that the reagent is applied in advance on at least part of the carrier.

Another application of the invention is a histamine detection reagent containing 2,3-naphathalene dicarboxylaldehyde.

The present invention is further directed to a food sanitation management method, which includes: a reaction step of causing an exudate or an extract of a food material or a food product, which is obtained in a process from collection of the food material to consumption of the food product, to react with 2,3-naphathalene dicarboxylaldehyde at pH of less than 10; and a detection step of detecting histamine based on a color change in said reaction step.

BEST MODES OF CARRYING OUT THE INVENTION

The histamine detection method of the invention includes a reaction step of causing a sample solution possibly containing histamine to react with 2,3-naphathalene dicarboxylaldehyde at PH of less than 10; and a detection step of detecting histamine based on a color change in the reaction step. There has been no study or report on the color reaction of histamine with 2,3-naphathalene dicarboxylaldehyde at pH of not higher than 8. It is known in the art that 2,3-naphathalene dicarboxylaldehyde reacts with a primary amine compound in the presence of cyan ion (CN—) at pH of not lower than 10 to produce a fluorescent substance (see B. K. Matuszewski, R. S. Givens, K. Srinivasachar, and R. G. Carlson, Anal. Chem. 59 (1987)). Reactions of 2,3-naphathalene dicarboxylaldehyde with amines in the absence of cyan ion at pH of lower than 10, however, have been totally unknown. The highly selective reaction of 2,3-naphathalene dicarboxylaldehyde with histamine to produce a compound with good color development has not been expected at all and is rather surprising.

The histamine detection method of this invention based on this new color reaction enables easier and quicker detection of histamine, compared with the conventional enzyme reaction-based measurement. This color reaction proceeds stably at significantly high speed and is stable even on a carrier, such as silica gel. The color reaction on the histamine-supportable carrier further facilitates the detection of histamine.

The histamine detection kit of the invention includes a 2,3-naphathalene dicarboxylaldehyde-containing reagent; and a reaction field providing module including a histamine-supportable carrier. The use of the histamine-supportable carrier enables the color reaction to proceed on the carrier with histamine supported thereon. This provides the histamine detection kit that attains easy and quick histamine detection with less number of instruments or devices for the detection. The histamine detection kit thus ensures easy and quick histamine detection in the process from collection of the food material to consumption of the food product.

The histamine detection method, the histamine detection kit, and the food sanitation management method of the invention are described below in detail with reference to some embodiments. In the following description, '%' and 'parts' respectively represent '% by weight' and 'parts by weight', unless otherwise specified.

(Histamine Detection Method)

(Detection Reagent)

Figure 1:
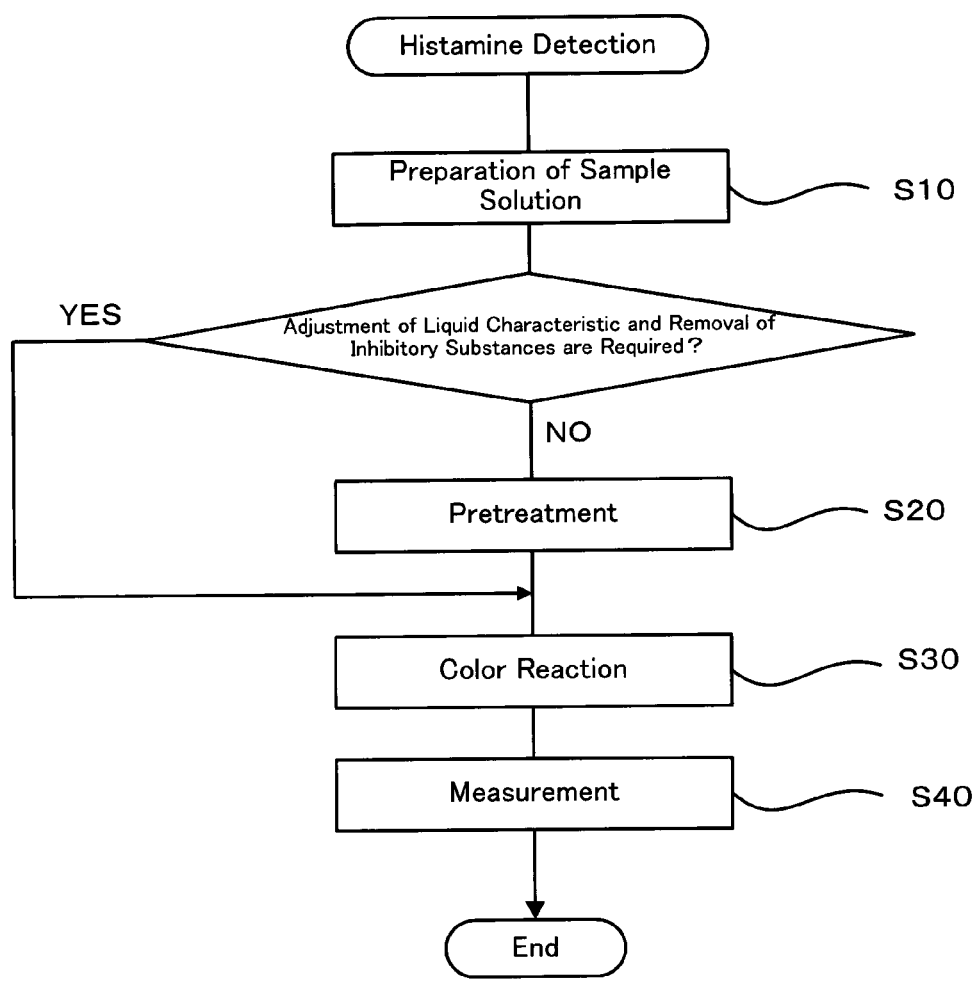
FIG. 1 is a flowchart showing a processing flow of histamine detection method.

The histamine detection method of the invention is described in detail with reference to the flowchart of FIG. 1.

(Detection Object)

The detection objects of the invention are samples having the potential for histamine content and include food products, human and animal samples, for example, blood samples and urine samples, and histamine-relevant drug screening samples. The preferable detection objects of the invention are food products having the high potential of histamine content, for example, meat and processed meat products, sea food and processed marine products, and various fermented food products. The meat and processed meat products include chicken meat, pig meat, and their canned, cooked, and half-cooked products. The sea food and processed marine products include fish, especially lean fish, for example, tuna, saury, bonito, horse mackerel, mackerel, swordfish, and flying fish, and canned, dried, and other half-cooked fish products. The fermented food products include soybean paste, soybean source, and wines.

(Preparation of Sample Solution) (Step S10)

The sample solution used in the histamine detection method of the invention may be the detection object, an exudate of the detection object, or an extract of the detection object by any suitable extraction technique. The exudate may be an exudate fluid exuded from the thawed or preserved meat or sea food or may be a liquid fraction obtained by solid-liquid separation of the ground or non-ground meat or sea food. The extract may be an extract fluid of the detection object, the ground detection object, or the exudate of the detection object in an adequate solvent.

When a food product is the detection object of the histamine detection method, only part or the whole of the food product may be used for preparation of the sample solution. For example, in fresh fish, fish meat having a high content of histidine as the precursor of histamine (the general meat region is preferable to the dark meat region) is desirable for preparation of the sample solution. In canned fish products, the whole canned food is desirable for preparation of the sample solution.

The solvent used for preparation of the extract may be any of histamine-soluble solvents including water, methanol, ethanol, propanol, 2-propanol, butanol, acetonitrile, trichloroacetic acid (TCA), and mixed solutions of water and one or multiple of these organic solvents. Methanol and aqueous TCA solution are especially preferable. Ethanol, 2-propanol, and other alcohols are preferably used for colored food products, such as soybean paste, soybean sauce, and wines. The alcohol extracts of these food products effectively elute the color component from silica or another carrier used as the color reaction field.

(Pretreatment for Color Reaction) (Step S20)

The sample solution, such as the exudate or the extract by solvent extraction, may directly be subjected to the color reaction as long as the sample solution has the liquid characteristic suitable for the color reaction and does not contain any inhibitory substances that may interfere with the color reaction. Otherwise the sample solution is pretreated to have the liquid characteristic suitable for the color reaction. The favorable conditions of the color reaction in the histamine detection method are an aqueous medium and pH controlled to be less than 10 or more specifically pH controlled to or below 8 (most preferably pH controlled to the range of 3 to 8). The sample solution is preferably pretreated to have such liquid characteristic, prior to the color reaction. The pretreatment enables the quick and easy color reaction of the sample solution by simple exposure to the reagent. Any of buffer solutions like phosphate buffer, inorganic acids like hydrochloric acid, organic acids, and alkalis like sodium hydroxide may be used for the pH control of the sample solution.

A column filled with an adequate carrier or a filter with the adequate carrier applied thereon may be used for extraction of histamine from the exudate or the extract to the aqueous medium. The extraction of histamine may otherwise take advantage of the difference in solubility among various solvents. One typical procedure feeds the exudate or the extract to an adequate carrier to make the histamine content in the exudate or the extract adsorbed or supported on the carrier, and washes the carrier with a suitably selected washing solvent. The procedure then feeds an eluting solvent to the carrier to elute the histamine content and uses the eluate of the histamine content as the sample solution. When an acid carrier is used, it is desirable to adjust the extract to the neutral or alkaline condition, before the supply of the extract to the carrier.

The carrier may be any of various organic polymers including cellulose, rayon, vinylon, polyester, nylon, and acrylic and various inorganic polymers including silica, although these examples are not restrictive in any sense. Since histamine has amino group, cation exchange resins having carbonate group or sulfonate group and acid carriers like silica are desirably used to readily support the histamine content thereon. The carrier may have any morphology to be formed in, for example, fibers, particles, or sheet. It is desirable to hold the carrier in a support structured to ensure easy supply of the extract. One preferable example of the support is a column, which is easily applicable to the carrier in any morphology, for example, fibers, particles, or sheet. The column to be filled with the carrier preferably has the externally visible transparency. The sheet carrier may be provide as a test sheet strip or any other suitable shape or may be further held on a frame-like base member for fixing at least part of the periphery of the sheet carrier.

For removal of the inhibitory substances, after the supply of the extract or the exudate, the carrier is washed with water or a phosphate buffer solution (for example, adjusted to about 0.2 M and pH 6 to 7). Aqueous hydrochloric acid may be used as the eluting solution used for elution of histamine from the carrier. This pretreatment step concentrates (purifies) the histamine content with removal of the inhibitory substances, prior to the color reaction. The carrier with the histamine content supported thereon may be used, without elution of histamine, as the reaction field for the subsequent color reaction, as described later.

(Color Reaction) (Step S30)

The histamine detection reagent used in the histamine detection method of the invention contains 2,3-naphathalene dicarboxylaldehyde as the coloring reactant. Any of 2,3-naphathalene dicarboxylaldehyde derivatives and analogs that react with histamine to show the equivalent or better color development may replace 2,3-naphathalene dicarboxylaldehyde. The histamine detection reagent contains 2,3-naphathalene dicarboxylaldehyde and a solvent, such as acetonitrile or methanol, for dissolution of 2,3-naphathalene dicarboxylaldehyde. The concentration of 2,3-naphathalene dicarboxylaldehyde is not specifically limited but is preferably to be approximately 1 mM, which ensures the good color development for the histamine concentration of or over 0.01 mM. The histamine detection reagent may include various additives, for example, an antiseptic or a stabilizer, according to the requirements.

(Reaction Conditions)

The histamine detection method of the invention takes advantage of the color reaction proceeding by exposure of the histamine content in the sample solution to 2,3-naphathalene dicarboxylaldehyde at pH of less than 10, specifically at pH of or below 9.5, more specifically at pH of not higher than 9 but not lower than 2.5, or most specifically at pH in the range of 3 to 8. The pH range of 3 to 8 gives the good color development. The pH range is preferably between 4 and 7. The color development may be insufficient to cause difficulty in visual detection at pH of less than 4 or at pH of higher than 7. The pH range is more preferably between 5 and 7. The color reaction proceeds at a high rate in the pH range of 5 to 7 to allow quick detection of the histamine content. The pH range is most preferably between 5 and 6. The color development is promptly stabilized in this pH range of 5 to 6 to enable the quick and highly accurate detection of the histamine content.

The pH condition is readily adjustable to the desired range by using a buffer solution, for example, phosphate buffer.

The reaction temperature is preferably in the range of not lower than 4° C. and not higher than 40° C., although this range is not restrictive in any sense. According to the inventors' experiments, the intensity of color development by the color reaction was independent of the temperature in this temperature range. The histamine detection method of the invention accordingly does not require the temperature control at ordinary temperatures. The reaction time is not specifically restricted. The color reaction proceeds very quickly and generally gives the visibly recognizable color development in 1 minute (this depends upon pH). The color development is stabilized in 5 to 30 minutes. The reaction time of not less than 1 minute may thus be set arbitrarily.

(Use of Carrier)

The carrier used for adjustment of the liquid characteristic or for concentration of the histamine content with removal of inhibitory substances possibly interfering with the color reaction may be used as the field of the color reaction with the histamine detection reagent. The supply of the histamine detection reagent to the carrier with histamine supported thereon causes the color reaction of histamine with 2,3-naphathalene dicarboxylaldehyde to proceed on the carrier. The procedure supplies an extract prepared as described above as the sample solution to a histamine-supportable cation exchange resin or silica carrier, washes out the inhibitory substances with an adequate washing solution, and adds the histamine detection reagent to the carrier with the histamine content supported thereon (with no elution of histamine from the carrier) to make the color reaction on the carrier. When the sample solution is supplied to the carrier after removal of the inhibitory substances, the washing step may be omitted. In this case, after pH adjustment when required, the procedure adds the histamine detection reagent to the carrier to make the color reaction on the carrier. In either case, the concentrated histamine content on the carrier reacts with the histamine detection reagent. When the carrier is in a visually recognizable condition, the color reaction gives the good color development (sufficient intensity of coloration) to allow easy visual detection of the histamine content. According to the inventors' experiments, the histamine content of about 0.05 mM was visually detected. The prompt color development is suitable for the quick and easy detection of the histamine content. The supply of the extract to the carrier enables simultaneous implementation of the pretreatment, for example, adjustment of the liquid characteristic, and the color reaction. This method is especially desirable for food products having the significant effects of inhibitory substances as the detection object. The carrier preferably has no color or white color for the better visual recognition of the color development.

The use of the carrier as the color reaction field is described more with reference to a concrete example. The procedure homogenizes a certain amount of fresh fish meat (raw fish), such as fresh tuna meat, adds an adequate amount of 5% aqueous TCA solution to the homogenized fish meat, and collects a liquid fraction or supernatant from the further homogenized mixture by solid-liquid separation or centrifugal separation. The procedure then adjusts pH to the range of 5 to 7 with an alkali, such as sodium hydroxide, to prepare a sample solution (including inhibitory substances). The prepared sample solution is supplied to an externally visible mini column filled with silica gel as the carrier. The carrier is washed with water and/or phosphate buffer at pH of 5.0 to 7.0, and the histamine detection reagent is added to the carrier. Histamine supported on the carrier is immediately exposed to the histamine detection reagent to make the color reaction and give the color development on the carrier. This method makes the concentrated histamine content supported on the carrier and thus ensures easy and highly sensitive visual recognition of the color development. This method allows purification of histamine and the color reaction to be carried out in an identical place at an extremely high speed, thus ensuring easy and quick detection of the histamine content.

In application of the carrier to detection of the histamine content in an alcohol extract of a colored food product, for example, soybean paste, soybean sauce, or wine, 2 to 5 carbon atom-containing alcohols, for example, ethanol, 2-propanol, butanol, or amyl alcohol, are preferably used as the washing solution. These 2 to 5 carbon atom-containing alcohols selectively remove the color components from the histamine-containing food extracts and thereby allow easy visual recognition of the histamine coloring reaction on the carrier.

(Measurement) (Step S40)

The color development by the color reaction of the histamine detection method is readily recognizable in a visible region, especially in a region of 500 nm to 750 nm. The color shade is easily observable with eyes. Even the eye observation enables quantitative analysis with some accuracy, as well as qualitative analysis. In instrumental determination of the absorbance, a detection wavelength for the absorbance is preferably selected in the range of 600 nm to 700 nm. The wavelength range of 600 nm to 700 nm enables the highly selective color development of histamine over other putrefactive polyamines, such as putrescine, cadaverine, and spermidine.

(Qualitative and Quantitative Analyses)

The histamine detection method of the invention is applicable to both qualitative analysis and quantitative analysis. The histamine detection method allows eye observation for the qualitative analysis. One applicable procedure of the quantitative analysis uses one or multiple standard solutions and prepares a standard curve of the absorbance at a preset wavelength. Another applicable procedure of the quantitative analysis measures the absorbance values or the absorbance coefficients at preset concentrations of histamine and determines the concentration of a sample solution based on the measured absorbance values or absorbance coefficients. The histamine detection method of the invention is applied to one or multiple histamine standard solutions of various histamine contents to give solutions of standard colors (standard solutions) or standard preparations (for example, carriers of standard colors). The use of such standard solutions enables the easy and quick quantitative analysis by eye observation.

The detection limit of histamine by the histamine detection method of the invention with the histamine standard solutions is approximately 0.01 mM. The amount of each collected detection object should be adequately determined to satisfy this detection limit. According to the inventors' experiments, the detection limit of histamine was at least 25 ppm for fresh tuna meat.

(Histamine Detection Kit)

The histamine detection kit embodying the histamine detection method of the invention described above may includes: a 2,3-naphathalene dicarboxylaldehyde-containing reagent; and a reaction field providing module including a histamine-supportable carrier. This histamine detection kit uses the carrier as the field for pretreatment and the color reaction of histamine to enable easy and quick detection of the histamine content. The 2,3-naphathalene dicarboxylaldehyde-containing reagent included in the histamine detection kit has the composition described above. The carrier used as the reaction field provided by the reaction field providing module has the structure described above. The reaction field providing module may have the histamine-supportable carrier alone or may have the histamine-supportable carrier held by an adequate supporting member. The reaction field providing module may have the carrier on at least one end thereof and a shape for holding function.

Figure 2:
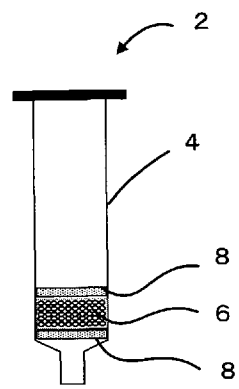
FIG. 2 shows one example of a reaction field providing module included in a histamine detection kit embodying the histamine detection method.
Figure 3:
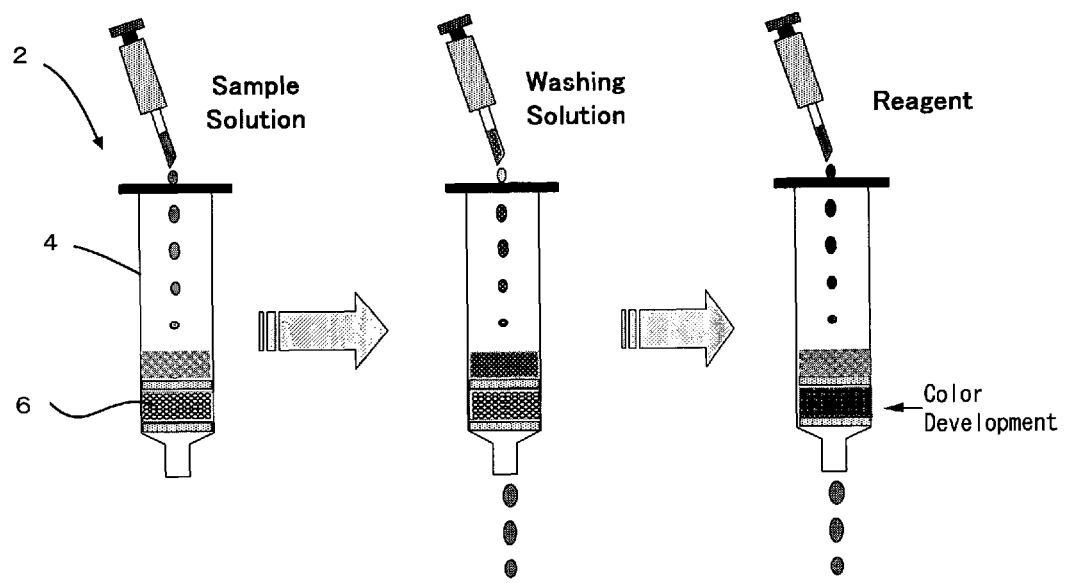
FIG. 3 shows a process of histamine detection with the reaction field providing module of FIG. 2.

In the reaction field providing module having the carrier alone, the carrier may be formed to a test sheet strip or any other suitable shape. The test sheet preferably has a holding member or is formed in a long strip to be readily held with fingers or tweezers. One reaction field providing module 2 formed in a column structure is shown in FIG. 2. The reaction field providing module 2 has a cylindrical column 4 of a transparent material filled with particles of a carrier 6. The carrier 6 may be placed between a pair of fibrous filters 8 of, for example, cellulose, in the column 4. FIG. 3 shows the pretreatment and the color reaction on the carrier 6 in the reaction field providing module 2. This illustrated example feeds a sample solution to the carrier 6 held in the reaction field providing module 2 of the column structure, washes the carrier 6 with an adequate washing solution, and adds the reagent to the carrier 6. The carrier 6 then gives color development for detection of the histamine content.

Figure 4:
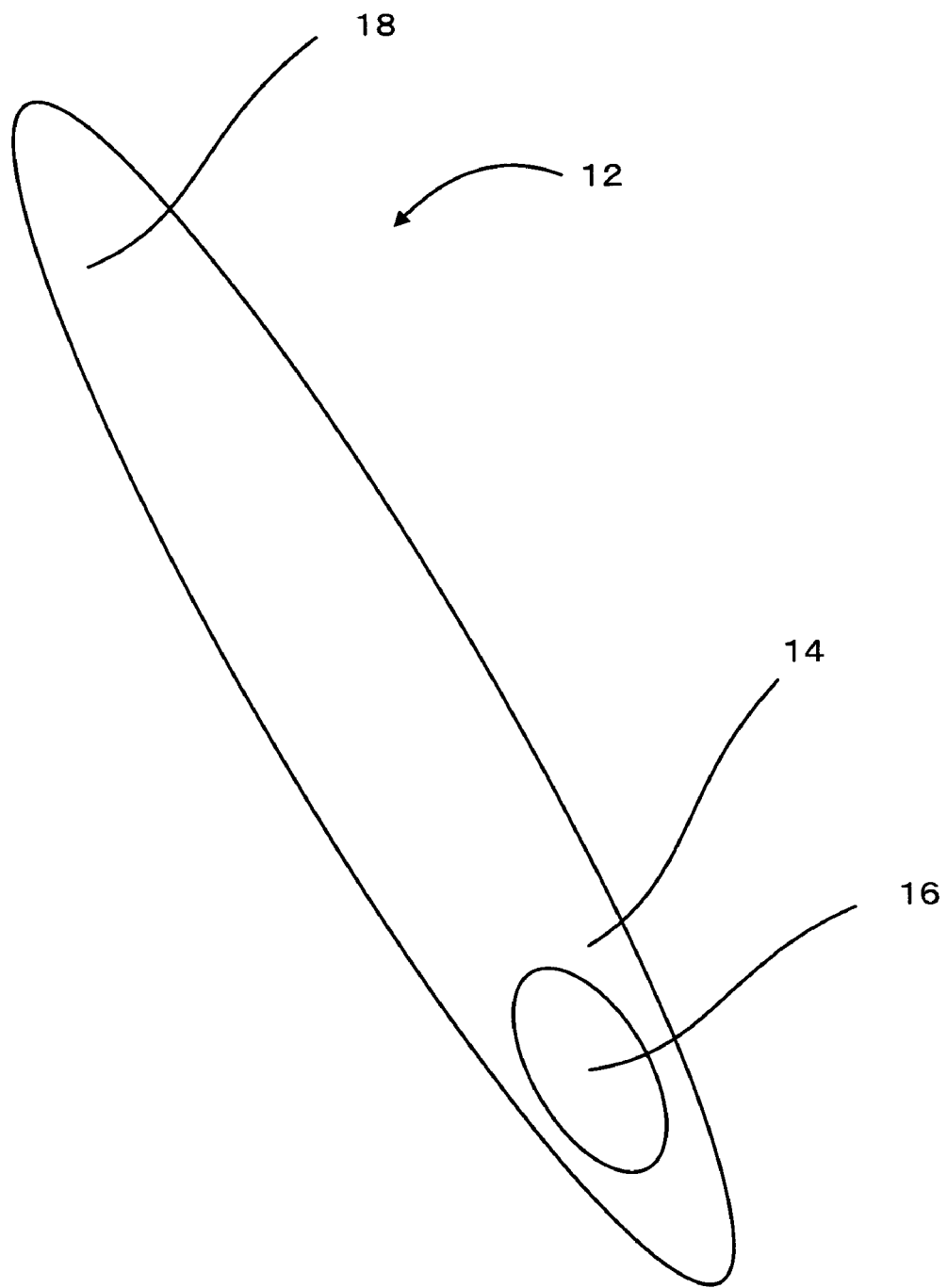
FIG. 4 shows another example of the reaction field providing module included in the histamine detection kit.

FIG. 4 shows another reaction field providing module 12 having a grip 18. The reaction field providing module 12 is a bar structure having a carrier 16 exposed on one end thereof and the grip 18 formed on the other end thereof The bar structure is made of plastic and has a frame 14 on its carrier supporting end to support the exposed carrier sheet 16. A sample solution is fed to the carrier sheet 16 exposed in the frame 14 to penetrate into the carrier sheet 16 and make the histamine content supported on the carrier sheet 16. The carrier sheet 16 held in the frame 14 may be formed to a filter that allows the outflow of the supplied and penetrated sample solution to only the other end opposite to its supply end. The other end of the sample solution opposite to the supply end may be blocked by part of the frame 14 or may have a reservoir for storing at least part of the sample solution.

In another example, the reaction field providing module is formed as part of a packaging container of food. In this structure, the carrier is an absorber that is isolated from the food and absorbs the exudate of the food. The carrier is placed in a specific site in the packaging container to allow penetration of the exudate of the food but to prevent the direct contact with the food. The carrier is preferably made of a semipermeable material to prevent the reverse flow of the exudate penetrated through the carrier to the food. The carrier is preferably designed to be visible from the outside of the packaging container or to be detachable from the packaging container. The reaction field providing module formed as part of the packaging container of the food enables easy detection of the histamine content in any stage of food preservation, distribution, and sale.

The reaction filed providing module of the column structure is desirably used for the sample solutions including inhibitory substances, which are to be removed prior to the color reaction. The reaction field providing module of the test sheet structure or of the frame structure is desirably used for the sample solutions after removal of inhibitory substances or for the sample solutions with the low potential for the presence of inhibitory substances.

The reagent may be kept in at least part of the carrier included in the reaction field providing module. This arrangement enables the quick color reaction on the carrier by simply feeding the sample solution to the carrier. The reagent may be kept in the carrier in any suitable form. For example, the reagent may be kept in part of the carrier to make a predetermined mark, such as 'no good', appear by exposure to histamine or similarly to make a predetermined barcode, which is readable by a barcode reader, appear by exposure to histamine. This mark or barcode appearing on the carrier by exposure to histamine allows easy detection of histamine. The machine reading of the mark or barcode attains the easy food sanitation management.

The amount of 2,3-naphathalene dicarboxylaldehyde kept in the carrier is adequately determined according to the required detection limit or another requirement.

(Food Sanitation Management Method)

The histamine detection method and the histamine detection kit of the invention are applicable to detect histamine in any stage of a manufacturing process of a food product and attain histamine-related sanitation management of the food product in the course from collection of its food material to consumption of the food product. The manufacturing process of the food product may include preservation, distribution, primary processing, secondary processing, and final processing of the food material. The food sanitation management method records the variation in histamine content or the measurement results of histamine detection relative to allowable maximum limits set in the respective stages for the purpose of sanitation management.

Histamine is used as the index of putrefaction. The histamine detection method and the histamine detection kit of the invention are thus applicable to check the freshness of food, especially meat, sea food, and their processed products, as well as to attain the sanitation management. The histamine detection method and the histamine detection kit of the invention are also applicable to allergy diagnosis with human urine and serum samples and to drug screening based on the histamine concentration as the index.

EXAMPLE 1

Some working examples of the invention are described below, although the invention is not restricted to these examples.

(1) Color Development of Histamine Against pH

The experiment of Example 1 prepared a 0.1 mM aqueous histamine solution, mixed 0.5 ml of the aqueous histamine solution with 2.5 ml of 0.1 M buffer solutions (with pH adjusted to 2, 4, 5, 6, 7, 8, and 9) and 0.5 ml of an acetonitrile solution of 1 mM 2,3-naphathalene dicarboxylaldehyde, and eye-observed the color development of the respective test solutions after 30 minutes. The results of eye observation of the respective test solutions showed practically no coloration at pH 2 and at pH 9, slight coloration at pH 8, and distinct coloration changing from green to blue green to orange in the pH range of 4 to 7.

Figure 5:
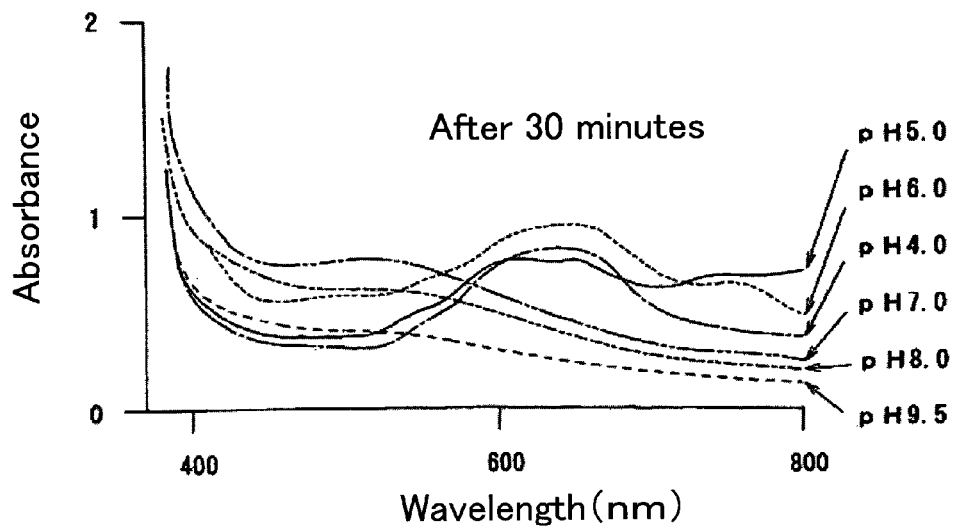
FIG. 5 shows absorption spectra of test solutions in a visible region.

Absorption spectra of test solutions prepared in the above manner by addition of 0.1 M buffer solutions (with pH adjusted to 4, 5, 6, 7, 8, and 9.5) were measured in a visible region after 30 minutes. The measurement results are shown in FIG. 5. Time variations of the absorbance at 610 nm were measured for test solutions prepared in the above manner by addition of 0.1 M buffer solutions (with pH adjusted to 2.5, 4, 5, 6, 7, 8, and 9.5). The measurement results are shown in FIG. 6.

As shown in FIG. 5, the absorption spectra of the test solutions adjusted to pH of or below 6 showed higher absorbance values and had their absorption maxima in the wavelength range of 500 nm to 800 nm or more specifically in the wavelength range of 600 nm to 700 nm. Especially the test solutions adjusted to pH of 5 and 6 had high absorbance values. The absorption spectra of the test solutions adjusted to pH of or above 7, on the other hand, showed significantly low absorbance values and did not have distinct absorption maxima in the above wavelength range. These measurement results well agree with the results of eye observation.

Figure 6:
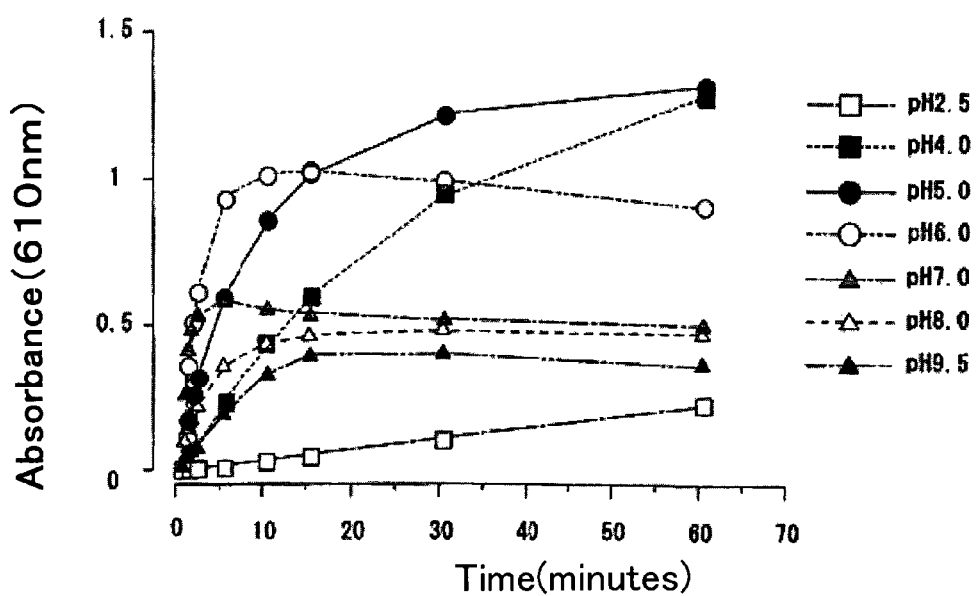
FIG. 6 shows time variations in absorbance of the test solutions (at 610 nm)

The absorbance values of the test solutions were not significantly varied but were rather stable for a time period from 10 minutes to 30 minutes after the preparation under any pH conditions as shown in FIG. 6. The test solutions showed higher absorbance values at pH 5 and 6 and had abrupt increases in absorbance within 10 minutes at pH 5, 6, and 7. This shows the favorable reaction pH of not lower than 2 but not higher than 9 or more specifically of not lower than 5 but not higher than 7. The pH adjustment to 5 to 6 was effective for quick and high-sensitive histamine detection.

A standard curve of histamine standard solutions in the concentration of 0.05 mM to 1.0 mM was prepared according to the measured absorbance values at the wavelength of 610 nm. The standard curve had a correlation factor 'r' of 0.997 and accordingly proved sufficient quantitative capability.

(2) Coloration of Amino Acids and Other Amines

The procedure first prepared 0.1 mM aqueous solutions of arginine (Arg), histidine, asparagine (Asn), serotonin (5-HT), cadaverine (Cad), spermidine (Spr), and histamine and a 1 mM aqueous solution of putrescine, mixed 0.5 ml aliquots of the respective aqueous solutions with 2.5 ml of 20 mM phosphate buffer (pH 5.0) and 0.5 ml of an acetonitrile solution of 1 mM 2,3-naphathalene dicarboxylaldehyde to prepare test solutions, and observed the color development of the respective test solutions after 30 minutes. The results of eye observation showed practically no coloration for the test solutions containing arginine, asparagine, and cadaverine, slight coloration for the test solutions containing histidine, serotonin, and spermidine, and distinct coloration for the test solutions containing putrescine (1 mM) and histamine.

Figure 7:
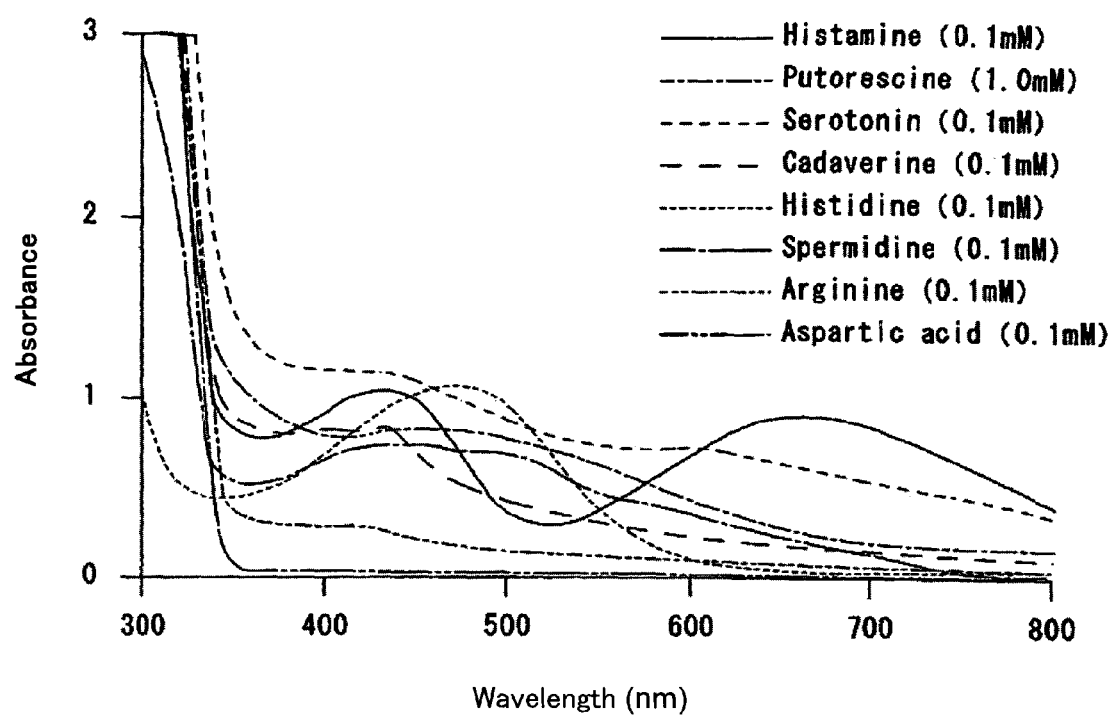
FIG. 7 shows absorption spectra of test solutions of various amines in the visible region.

FIG. 7 shows measured absorption spectra of these test solutions in the visible region. Only serotonin had relatively high absorbance values in the wavelength range of 600 nm to 700 nm, where histamine had high absorbance values. The other inhibitory polyamines (spermidine and putrescine) possibly interfering with histamine had sufficiently low absorbance values. Serotonin is a human-derived protein and is generally not found in food. In the histamine detection method of the invention, the color reaction gives the selectively high color development with regard to various amino group-containing compounds. The high purification of histamine ensures the measurement of high accuracy, while the relatively low purification of histamine enables the measurement of certain accuracy.

EXAMPLE 2

(Experiment With Real Sample)

The experiment was performed by addition of a histamine standard preparation to a real sample of fresh fish meat (commercially available raw tuna). The histamine standard preparation used was histamine dihydrochloride (special grade chemical manufactured by Wako Pure Chemical Industries, Ltd.), and the histamine detection reagent used was a 1 mM acetonitrile solution of 2,3-naphathalene dicarboxylaldehyde (manufactured by Sigma-Aldrich).

The procedure weighed 5 g of commercially available fresh raw tuna in a homogenizer (Nihon Seiki Co., Ltd.), added 25 ppm, 50 ppm, and 100 ppm aqueous solutions of the histamine standard preparation and 30 ml of a 5% aqueous TCA solution, and homogenized the respective mixtures for 1 minute. After centrifugation of each of the homogenized solutions at 4° C., 1000 rpm (himac CR-20 manufactured by Hitachi Koki Co., Ltd.), 1000 μl of the supernatant was mixed with 250 μl of a 1 M sodium hydroxide solution with stirring to give a TCA-extracted sample solution. The TCA-extracted sample solutions had pH of 8. Methanol-extracted sample solutions were prepared by the similar procedure with replacement of the aqueous TCA solution by methanol and with addition of 20 μl of the 1 M sodium hydroxide solution in place of 250 μl. The methanol-extracted sample solutions had pH of 7.

A histamine detection column was prepared as a histamine detection cartridge by filling a commercially available 1 ml injection syringe (for tuberculin, manufactured by Terumo Corporation) with approximately 50 mg of silica gel (Silica Gel 60 manufactured by Merck Ltd., 1.07734, 1000) as the carrier. The carrier was charged into the bottom of the syringe with little amounts of absorbent cotton as upper and lower sealing members.

The procedure introduced 500 μl of each sample solution to the histamine detection cartridge and applied pressure to the carrier with a piston of the injection syringe to make the sample solution pass through the carrier. The procedure then similarly introduced 500 μl of each sample solution to the cartridge under pressure to make the sample solution pass through the carrier, sequentially introduced one 200 μl aliquot of a 0.2 M phosphate buffer (pH 6.0) and four 200 μl aliquots of water to the cartridge to wash the carrier, and subsequently introduced 200 μl of the histamine detection reagent to make the reagent pass through the carrier in the similar manner.

The color of the carrier was observed with eyes 1 minute after the transmission of 200 μl of the reagent. The distinct color development was visually recognized with regard to the sample solution containing 25 ppm histamine standard preparation. There was practically no color fading even after 6 hours. The similar results were obtained irrespective of the solvent used for extraction, that is, TCA and methanol. According to the results of this experiment, the histamine detection cartridge had the histamine detection limit of 25 ppm and the required reaction time was 1 minute for eye observation of the histamine detection at the 25 ppm level.

The invention claimed is:

1. A histamine detection method, comprising:
a reaction step of providing a sample solution possibly containing histamine the addition of 2,3-napthalene dicarboxylaldehyde to the sample solution and, if histamine is present, reacting the histamine in the sample solution with 2,3-naphathalene dicarboxylaldehyde in an absence of $CN^-$ ions at pH of less than 10; and
a detection step of detecting histamine based on a color change in said reaction step.

2. A histamine detection method in accordance with claim 1, wherein said detection step detects the histamine at wavelengths of not lower than 600 nm and not higher than 700 nm.

3. A histamine detection method in accordance with claim 1, said histamine detection method further comprising:
a supply step of feeding the sample solution to a histamine-supportable carrier, prior to said reaction step.

4. A histamine detection method in accordance with claim 3, wherein in said reaction step, if histamine is present in the sample solution, reacting the histamine with 2,3-naphathalene dicarboxylaldehyde on the carrier.

5. A histamine detection method in accordance with claim 1, wherein the sample solution is either of a fish meat exudate or a fish meat extract.

6. A histamine detection method in accordance with claim 1, wherein said detection step determines quantity of histamine corresponding to a level of the color change.

7. A food sanitation management method, comprising:
a reaction step of providing an exudate or an extract of a food material or a food product, which possibly contains histamine and is obtained in a process from collection of the food material to consumption of the food product adding 2,3-napthalene dicarboxylaldehyde to the sample solution, and if histamine is present, reacting the histamine with 2,3-naphthalene dicarboxylaldehyde in an absence of $CN^-$ ions, at pH of less than 10; and
a detection step of detecting histamine based on a color change in said reaction step.

8. A histamine detection method in accordance with claim 1, wherein the pH is in the range of 3 to 8.

9. A histamine detection method in accordance with claim 1, wherein the pH is in the range of 4 to 7.

* * * * *